(12) United States Patent
Swisher et al.

(10) Patent No.: US 8,121,785 B2
(45) Date of Patent: Feb. 21, 2012

(54) BICYCLE COMPUTER HAVING POSITION-DETERMINING FUNCTIONALITY

(75) Inventors: Sarah L. Swisher, Overland Park, KS (US); John H. Lovitt, Spring Hill, KS (US); Claudette D. Stevenson, Wilsonville, OR (US); David J. Downey, Louisburg, KS (US)

(73) Assignee: Garmin Switzerland GmbH (CH)

( * ) Notice: Subject to any disclaimer, the term of this patent is extended or adjusted under 35 U.S.C. 154(b) by 949 days.

(21) Appl. No.: 11/965,318

(22) Filed: Dec. 27, 2007

(65) Prior Publication Data

US 2009/0063049 A1  Mar. 5, 2009

Related U.S. Application Data

(60) Provisional application No. 60/968,557, filed on Aug. 28, 2007.

(51) Int. Cl.
| | |
|---|---|
| G01C 21/00 | (2006.01) |
| G01C 21/26 | (2006.01) |
| G01C 21/30 | (2006.01) |
| G01C 21/34 | (2006.01) |

(52) U.S. Cl. ........................... 701/211; 701/213
(58) Field of Classification Search .................. None
See application file for complete search history.

(56) References Cited

U.S. PATENT DOCUMENTS

| | | | |
|---|---|---|---|
| 5,847,641 A | 12/1998 | Jinbo | 340/432 |
| 6,450,922 B1 | 9/2002 | Henderson et al. | 482/8 |
| 6,463,385 B1 * | 10/2002 | Fry | 701/213 |
| 6,790,178 B1 | 9/2004 | Mault et al. | 600/300 |
| 6,837,827 B1 | 1/2005 | Lee et al. | 482/8 |
| 6,885,971 B2 | 4/2005 | Vock et al. | 702/182 |
| 7,132,931 B2 | 11/2006 | Okada | 340/427 |
| 7,254,516 B2 | 8/2007 | Case, Jr. et al. | 702/182 |
| 7,585,252 B2 * | 9/2009 | Alexanderson | 482/9 |
| 7,715,982 B2 * | 5/2010 | Grenfell et al. | 701/213 |
| 2003/0186784 A1 | 10/2003 | Ogawa | 482/8 |
| 2004/0117072 A1 * | 6/2004 | Takeda | 701/1 |
| 2004/0152961 A1 * | 8/2004 | Carlson et al. | 600/301 |
| 2005/0113650 A1 | 5/2005 | Pacione et al. | 600/300 |
| 2005/0233861 A1 | 10/2005 | Hickman et al. | 482/8 |
| 2006/0136173 A1 * | 6/2006 | Case et al. | 702/182 |
| 2008/0103794 A1 * | 5/2008 | Pettiross et al. | 705/1 |
| 2009/0270689 A1 * | 10/2009 | Galland | 600/300 |

FOREIGN PATENT DOCUMENTS

| | | |
|---|---|---|
| JP | 2000-198481 | 7/2000 |
| KR | 200434483 | 12/2006 |

OTHER PUBLICATIONS

Printout from http://www.paraos.co.kr/english//Paroas%20G-100_E_manual_1.pdf 40 pages, published Aug. 2005.
Office Action dated Feb. 15, 2008 from U.S. Appl. No. 11/232,151, filed Sep. 21, 2005.

(Continued)

Primary Examiner — Michael J. Zanelli
(74) Attorney, Agent, or Firm — Samuel M. Korte

(57) ABSTRACT

A bicycle computer having position-determining functionality is described. In an implementation, an apparatus includes a housing configured to attach to a bicycle. The apparatus has one or more modules to store training metrics of a user of the bicycle as a function of geographic position.

15 Claims, 7 Drawing Sheets

OTHER PUBLICATIONS

Garmin Forerunner 201 Personal Trainer Owner's Manual, Oct. 2003, see p. 10.
Office Action dated May 13, 2008 from U.S. Appl. No. 11/232,151, filed Sep. 21, 2005.
Office Action dated Sep. 11, 2008 from U.S. Appl. No. 11/232,151, filed Sep. 21, 2005.
International Search Report from corresponding International Application No. PCT/US2008/066097, dated Nov. 25, 2008.
Printout from http://quark.us/index.php?option=com_context&task=view&id=13&Itemid=29 , 3 pages, printed Aug. 20, 2007.
Garmin's Edge 205/305 Owner's Manual, Dec. 2005.
Office Action dated Nov. 28, 2009, from U.S. Appl. No. 11/218,845, filed Sep. 2, 2005.

* cited by examiner

BICYCLE COMPUTER HAVING POSITION-DETERMINING FUNCTIONALITY

CROSS-REFERENCE TO RELATED APPLICATIONS

The present application claims the benefit under 35 U.S.C. 119(e) of U.S. Provisional Patent Application Ser. No. 60/968,557, filed Aug. 28, 2007, which is herein incorporated by reference in its entirety.

BACKGROUND

Bicycle computers are used by a wide range of users for a variety of different purposes. For example, a casual user may be curious about the fastest-speed attainable on a downhill course and therefore use a speedometer to determine this maximum speed. More serious users may use bicycle computers to obtain additional information, such as distance traveled and so on. Traditional bicycle computers, however, were often limited by the information that may be obtained.

Further, traditional techniques to obtain information on a bicycle relied on a variety of different devices to obtain and output data separately, such as a speedometer and a heart rate monitor. Therefore, the user may be forced to use a multitude of different devices to obtain desired information. Further, because these devices were implemented separately, the devices could not share and leverage this information, one to another.

SUMMARY

A bicycle computer having position-determining functionality is described. In an implementation, an apparatus includes a housing configured to attach to a bicycle. The apparatus has one or more modules to store training metrics of a user of the bicycle as a function of geographic position. In another implementation, a geographic position of a bicycle computer is determined. A virtual training partner is output, having one or more training metrics, by the bicycle computer based on the determined geographic position.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are exemplary and explanatory only and are not necessarily restrictive of the invention claimed. The accompanying drawings, which are incorporated in and constitute a part of the specification, illustrate embodiments of the invention and together with the Detailed Description, serve to explain the principles of the invention.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different instances in the description and the figures may indicate similar or identical items.

DETAILED DESCRIPTION

Figure 1:
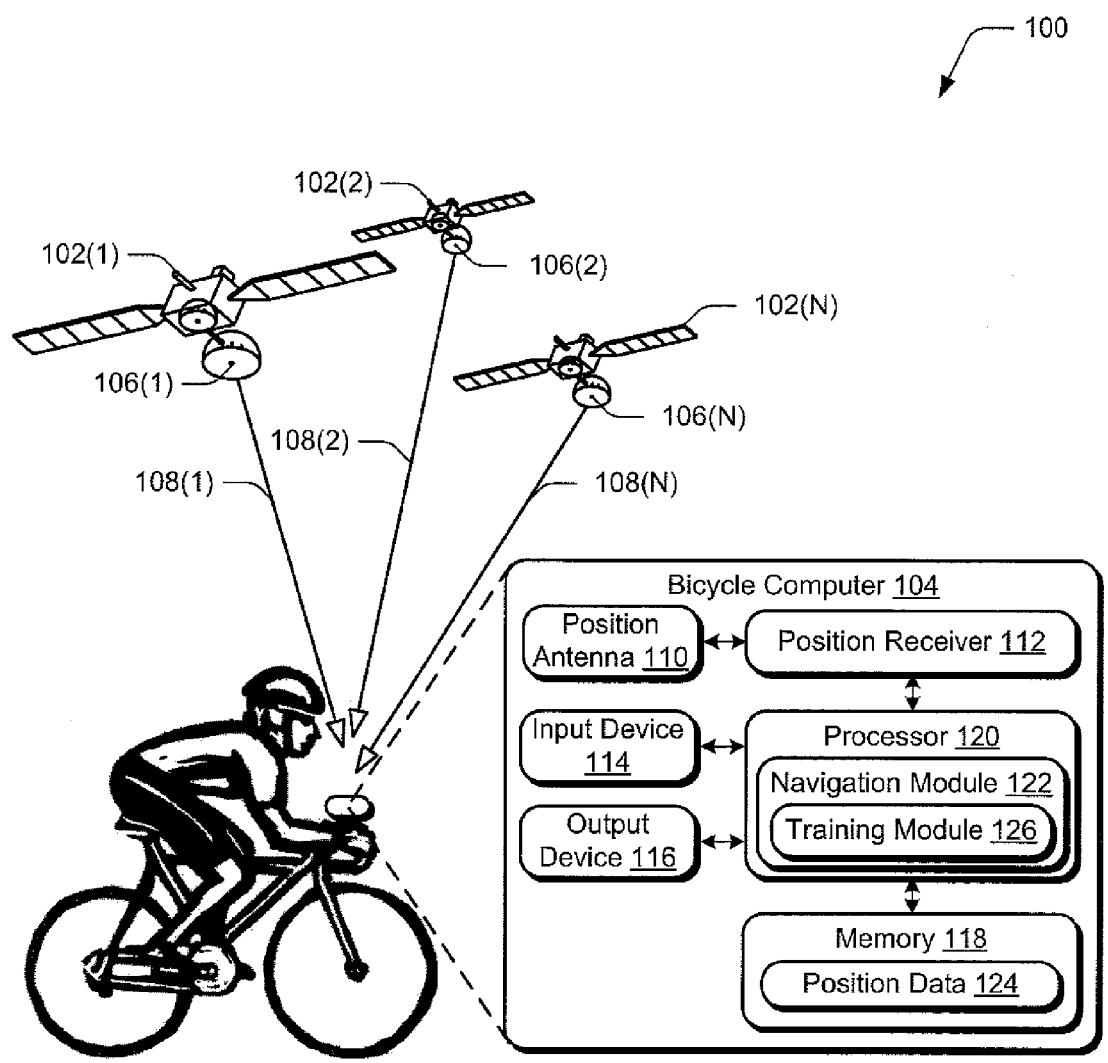
FIG. 1 is an illustration of an environment in an exemplary implementation that is operable to employ a bicycle computer having position-determining functionality.

Bicyclists may use a variety of devices to gauge and plan their workouts, and to make cycling more enjoyable. However, these devices were typically provided separately and had limited functionality such that information between the devices was not shared and therefore could not be leveraged by other devices.

In one or more implementations, a bicycle computer having position-determining functionality is described. For example, a bicycle computer may include Global Positioning System (GPS) functionality to provide positional awareness, such as through output of a map including a current position, destination, and so on. The bicycle computer may also combine this functionality with training metrics of a user (e.g., heart rate, power, cadence, and so on) to track the user's training regimen. For instance, the bicycle computer may store data at predetermined intervals which indicates a current geographical position, speed, time, and one or more of the training metrics such as heart rate.

The combination of GPS mapping with training metrics allows the user to see their speed, heart rate, power, and so on as a function of position, which creates entirely new ways to plan and analyze activities. For example, an activity log displayed on the bicycle computer's map screen may indicate heart rate and/or power output zones using color variation. Metrics displayed on the bicycle computer could also be color-coded to indicate intensity or training zones. The combination of training data and specific location enables cyclists to better analyze their performance and design tailored training plans to achieve their goals.

The position-determining functionality may also be leveraged to provide a "virtual training partner" on the bicycle computer. For example, a bicyclist may desire to ride a relatively hilly course under a desired amount of time. To compute a pace that would meet this goal, the total course length may be divided by the desired amount of time to compute an average pace. However, this average pace does not take into account the hills in the course. Therefore, the pace of the bicyclist may vary greatly to meet this goal, whereas the average does not. By using position-determining functionality, the virtual training partner may be configured to take into account terrain that is to be encountered on the desired course. This information may be obtained in a variety of ways, such as from a previous ride, a download obtained via a network connection, and so on. In this way, a user is provided with a virtual training partner that better reflects the terrain to be encountered, further discussion of which may be found in relation to FIGS. 4 and 6.

In the following discussion, an exemplary bicycle computer environment and system is first described in relation to FIGS. 1 and 2. An exemplary bicycle computer is then shown in relation to FIGS. 3 and 4 which may be employed in the exemplary environment. Exemplary procedures are then shown in relation to FIGS. 5 and 6 which may be implemented in the exemplary environment by the exemplary bicycle computers, as well as by other bicycle computers having position-determining functionality.

FIG. 1 illustrates an environment 100 having an exemplary bicycle computer that incorporates positioning-system functionality. A variety of positioning systems may be employed to provide position-determining techniques, an example of which is illustrated in FIG. 1 as a Global Positioning System (GPS) although other techniques are also contemplated such as GNSS. The environment 100 can include any number of position-transmitting platforms 102(1)-102(N), such as a GPS platform, a satellite, a retransmitting station, an aircraft, and/or any other type of positioning-system-enabled transmission device or system. The environment 100 also includes a bicycle computer 104, which is illustrated as being attached to a bicycle of a bicyclist. Although a GPS system is described and illustrated in relation to FIG. 1, it should be apparent that a wide variety of other positioning systems may also be employed, such as terrestrial based systems (e.g., wireless-phone based systems that broadcast position data from cellular towers), wireless networks that transmit positioning signals, and so on. For example, positioning-determining functionality may be implemented through use of a server in a server-based architecture, from a ground-based infrastructure, through one or more sensors (e.g., gyros, odometers, magnetometers), through one or more bicycle mounted sensors (e.g., wheel speed sensor, power meters or power sensors), use of "dead reckoning" techniques, and so on.

In the environment 100 of FIG. 1, the position-transmitting platforms 102(1)-102(N) are depicted as GPS satellites which are illustrated as including one or more respective antennas 106(1)-106(N). The one or more antennas 106(1)-106(N) each transmit respective signals 108(1)-108(N) that may include positioning information (e.g., timing signals, navigation signals, and so on) to the bicycle computer 104. Although three position-transmitting platforms 102(1)-102(N) are illustrated, it should be readily apparent that the environment may include additional position-transmitting platforms 102(1)-102(N) to provide additional position-determining functionality, such as redundancy and so forth. For example, the three illustrated position-transmitting platforms 102(1)-102(N) may be used to provide two-dimensional navigation while four position-transmitting platforms may be used to provide three-dimensional navigation. A variety of other examples are also contemplated, including use of terrestrial-based transmitters as previously described.

Position-determining functionality, for purposes of the following discussion, may relate to a variety of different navigation techniques and other techniques that may be supported by "knowing" one or more positions. For instance, position-determining functionality may be employed to provide location information, timing information, speed information, and a variety of other navigation-related data. Accordingly, the bicycle computer 104 may be configured in a variety of ways to perform a wide variety of functions. For example, the bicycle computer 104 may be configured for on-road navigation through the use of turn-by-turn instructions, off-road navigation by providing detailed information on trails and terrain features, and so forth. Accordingly, the bicycle computer 104 may include a variety of devices to determine position using one or more of the techniques previously described.

The illustrated bicycle computer 104 of FIG. 1 includes a position antenna 110 that is communicatively coupled to a position receiver 112. The position receiver 112, an input device 114 (e.g., a touch screen, buttons, microphone, wireless input device, data input, and so on), an output device 116 (e.g., a color screen, speakers and/or data connection) and a memory 118 are also illustrated as being communicatively coupled to a processor 120. A variety of different input devices 114 may be employed by the bicycle computer 104, such as to obtain training metrics which may be discussed in greater detail in relation to FIG. 2.

The processor 120 is not limited by the materials from which it is formed or the processing mechanisms employed therein, and as such, may be implemented via semiconductor(s) and/or transistors (e.g., electronic integrated circuits (ICs)), and so forth. Additionally, although a single memory 118 is shown, a wide variety of types and combinations of memory may be employed, such as random access memory (RAM), hard disk memory, removable medium memory (e.g., the memory 118 may be implemented via a slot that accepts a removable memory cartridge such as an SD card and so on), and other types of computer-readable media.

Although the components of the bicycle computer 104 are illustrated separately, it should be apparent that these components may also be further divided (e.g., the output device 116 may be implemented as speakers and a display device) and/or combined (e.g., the input and output devices 114, 116 may be combined via a touch screen) without departing from the spirit and scope thereof. Thus, the components illustrated in FIG. 1 are just one of a variety of different implementations that may be employed by the bicycle computer 104.

The illustrated position antenna 110 and position receiver 112 are configured to receive the signals 108(1)-108(N) transmitted by the respective antennas 106(1)-106(N) of the respective position-transmitting platforms 102(1)-102(N). These signals are provided to the processor 120 for processing by a navigation module 122, which is illustrated as being executed on the processor 120 and is storable in the memory 118. The navigation module 122 is representative of functionality that determines a geographic location, such as by processing the signals 108(1)-108(N) obtained from the position-transmitting platforms 102(1)-102(N) to provide the position-determining functionality previously described, such as to determine location, speed, time, and so forth.

The navigation module 122, for instance, may be executed to use position data 124 stored in the memory 118 to generate navigation instructions (e.g., turn-by-turn instructions to an input destination), show a current position on a map, and so on. The navigation module 122 may also be executed to provide other position-determining functionality, such as to determine a current speed, calculate an arrival time, and so on. A wide variety of other examples are also contemplated.

The navigation module 122 is also illustrated as including a training module 126, which is representative of functionality of the bicycle computer 104 involving training metrics. As previously described, the navigation module 122 may be utilized to implement position-determining functionality, such as to determine a current geographical position of the bicycle computer 104. The current geographical position may then be output in a variety of ways, such as in conjunction with a map, further discussion of which may be found in relation to FIG. 3.

The training module 126 may be implemented to collect training metrics regarding use of the bicycle by a user. These training metrics may then be stored (e.g., at predetermined intervals) as a function of geographic position determined by the navigation module 122, which may be utilized to provide a wide variety of functionality. For example, the stored training metrics may be utilized to provide a detailed training log that may be output by the bicycle computer 104 that not only shows the training metrics (e.g., heart rate, cadence, power, and so on) but also where those training metrics were encountered, i.e., the geographic position recorded for those metrics. In this way, the user may increase training efficiency by identifying areas of strength (e.g., hill climbs) and weakness (e.g., resting on downhill terrain) and adjust accordingly.

The training module 126 may also be representative of functionality to provide a "virtual training partner". For example, the user may have previously ridden a particular course and had data stored that describes training metrics as a function of geographic position. This data may then be output during a subsequent ride by the user (or another user) as a virtual training partner in conjunction with the user's current training metrics. Thus, the user may make a comparison of a current ride with a previous ride to determine if they are improving or regressing. Additionally, in an implementation the stored training metrics may be aggregated over a number of rides of a particular course (which may be user selectable) for comparison to an average, e.g., the last ten rides.

In another example, a virtual training partner may be downloaded for comparison. For instance, the user may access a website and download a profile of the last winner of the Tour de France over a particular course to make a comparison with a world class athlete. In another instance, users may share profiles of training metrics as a function of geographic position with each other, such as to engage in friendly competition. A variety of other uses of a virtual training partner are contemplated, further discussion of which may be found in relation to FIGS. 4 and 6.

Generally, any of the functions described herein can be implemented using software, firmware, hardware (e.g., fixed logic circuitry), manual processing, or a combination of these implementations. The terms "module," "functionality," and "logic" as used herein generally represent software, firmware, or a combination of software and firmware. In the case of a software implementation, the module, functionality, or logic represents program code that performs specified tasks when executed on a processor (e.g., CPU or CPUs). The program code can be stored in one or more computer readable memory devices, e.g., the memory 118 of FIG. 1. The features of the position-determining techniques as implemented by a bicycle computer described below are platform-independent, meaning that the techniques may be implemented on a variety of commercial computing platforms having a variety of processors.

Figure 2:
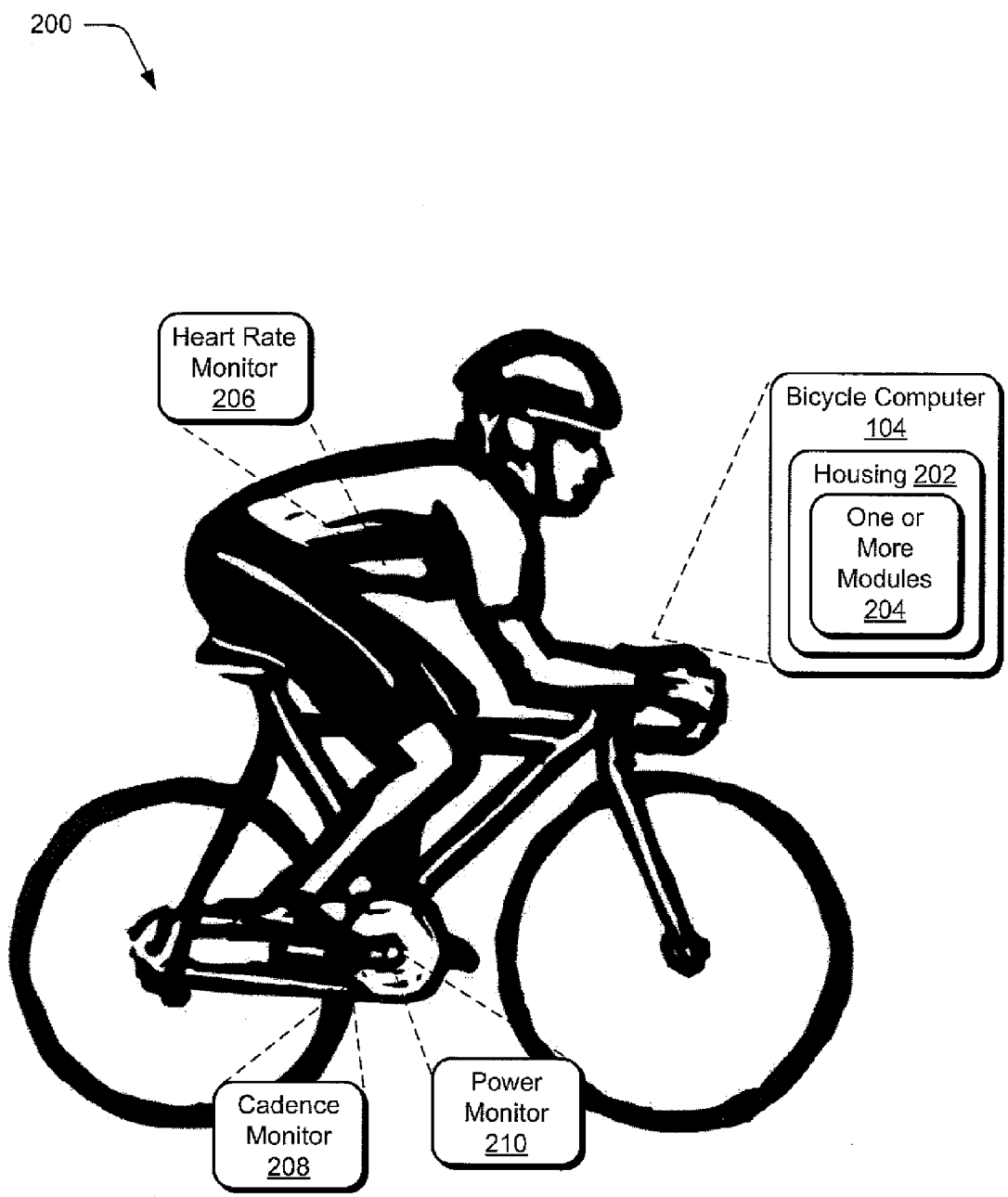
FIG. 2 is an illustration of a system including an exemplary implementation of the bicycle computer of FIG. 1 as being in wireless communication with a plurality of devices configured to provide training metrics of a user of a bicycle.

FIG. 2 illustrates an exemplary implementation of a system 200 that includes the bicycle computer 104 of FIG. 1 as being in wireless communication with a plurality of devices configured to provide training metrics of a user of a bicycle. The bicycle computer 104 is illustrated as including a housing 202 that includes one or more modules 204, such as the navigation module 122 and training module 126 of FIG. 1. The housing 202 may be configured in a variety of ways, such as a weather and/or water resistant shell to protect circuitry and power supply used to implement the one or more modules 204.

The bicycle computer 104 in the system 200 of FIG. 2 is in wireless communication with a plurality of devices configured to collect information regarding training metrics of a user of the bicycle. For example, a heart rate monitor 206 may collect information regarding the beats per minute of the user's heart, which may be communicated wirelessly to the bicycle computer 104. In another example, a cadence monitor 208 may count a cadence of the user through revolutions of the pedals and/or front sprocket. In yet another example, a power determining device may be used to measure, calculate or estimate the power of the user. For instance, in one implementation, a power monitor 210 may be placed within the crank set of the bicycle to measure power of the user, such as in watts. A variety of other training metric examples of a user are also contemplated, such as a speed sensor.

The training metrics collected by the bicycle computer 104 may then be stored as a function of geographic position. For example, the one or more modules 204 may determine a current geographic position at a predetermined interval (e.g., each second) through the use of GPS functionality. The training metrics may then be stored as a function of the current geographic position, such as to form a training log, configure a virtual training partner, and so on. Training metrics can also be stored without geographic position data, such as in areas where GPS is not available (e.g., when training inside of a building).

Other metrics may also be collected by the bicycle computer 104 (either directly by the computer itself and/or wirelessly from other devices) and stored as a function of geographic position. For example, the bicycle computer 104 may determine speed, incline, altitude gain, timing, and so on of a track. These metrics may also be stored as a function of geographic position and leveraged in a variety of ways, such as to configure a future training program, virtual training partner, and so forth. These metrics can also be stored without geographic position data, such as in areas where GPS is not available (e.g., when training inside of a building).

This information (e.g., the training metrics and/or other metrics) may be stored in a variety of ways. For instance, an activity-based scheme may be employed to define a training route that includes a plurality of tracked geographical points. The user may then access this route at a later time, such as automatically when the bicycle computer 104 is at a similar geographical location along the route, through a menu of stored routes, and so on. Thus, this activity-based scheme may provide an alternate to a purely position-based scheme, although such schemes are also contemplated.

Figure 3:
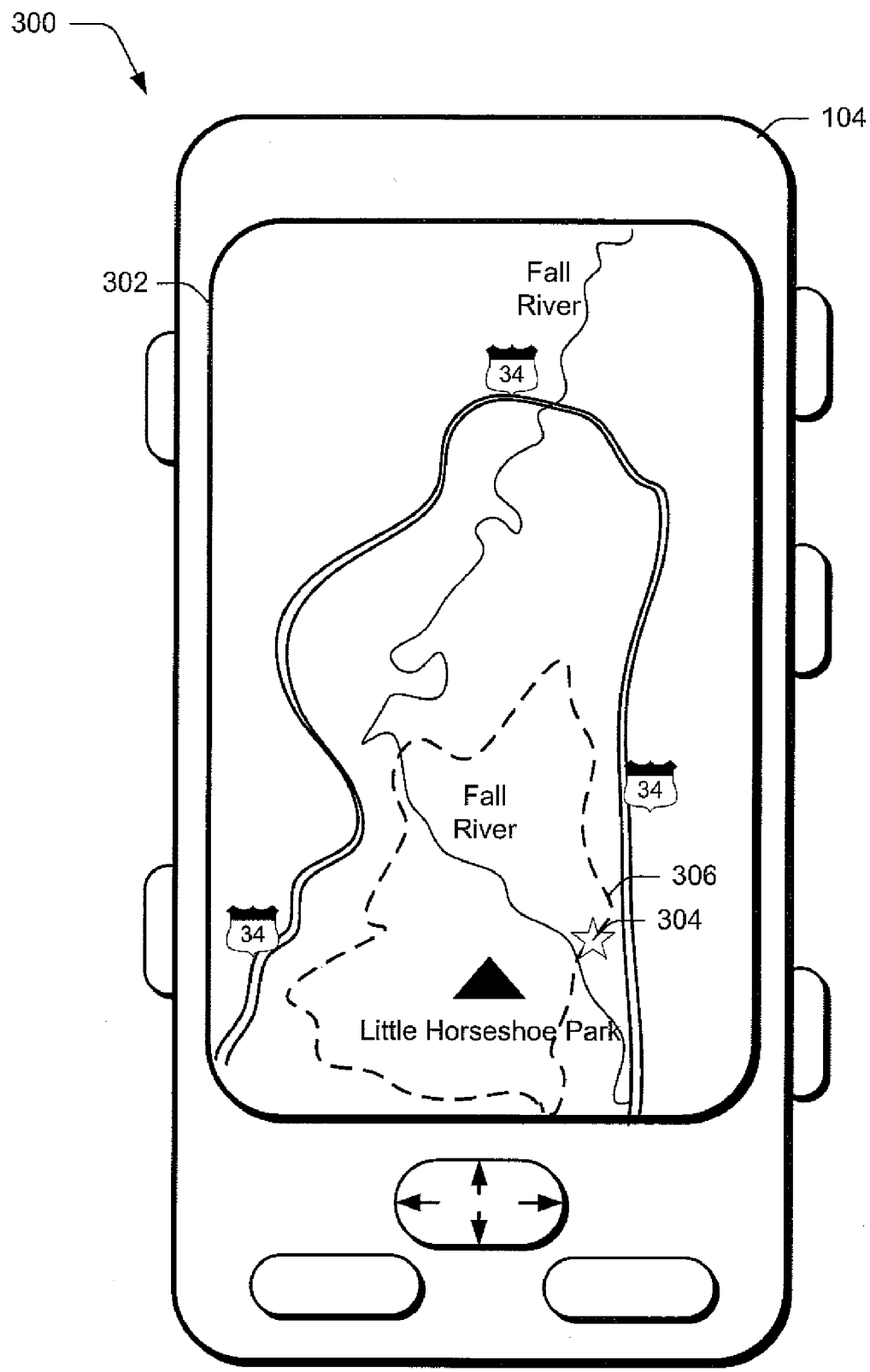
FIG. 3 is an illustration of an exemplary implementation of the bicycle computer of FIGS. 1 and 2 as outputting a map that includes a current geographical position of the bicycle computer and a track.
Figure 4:
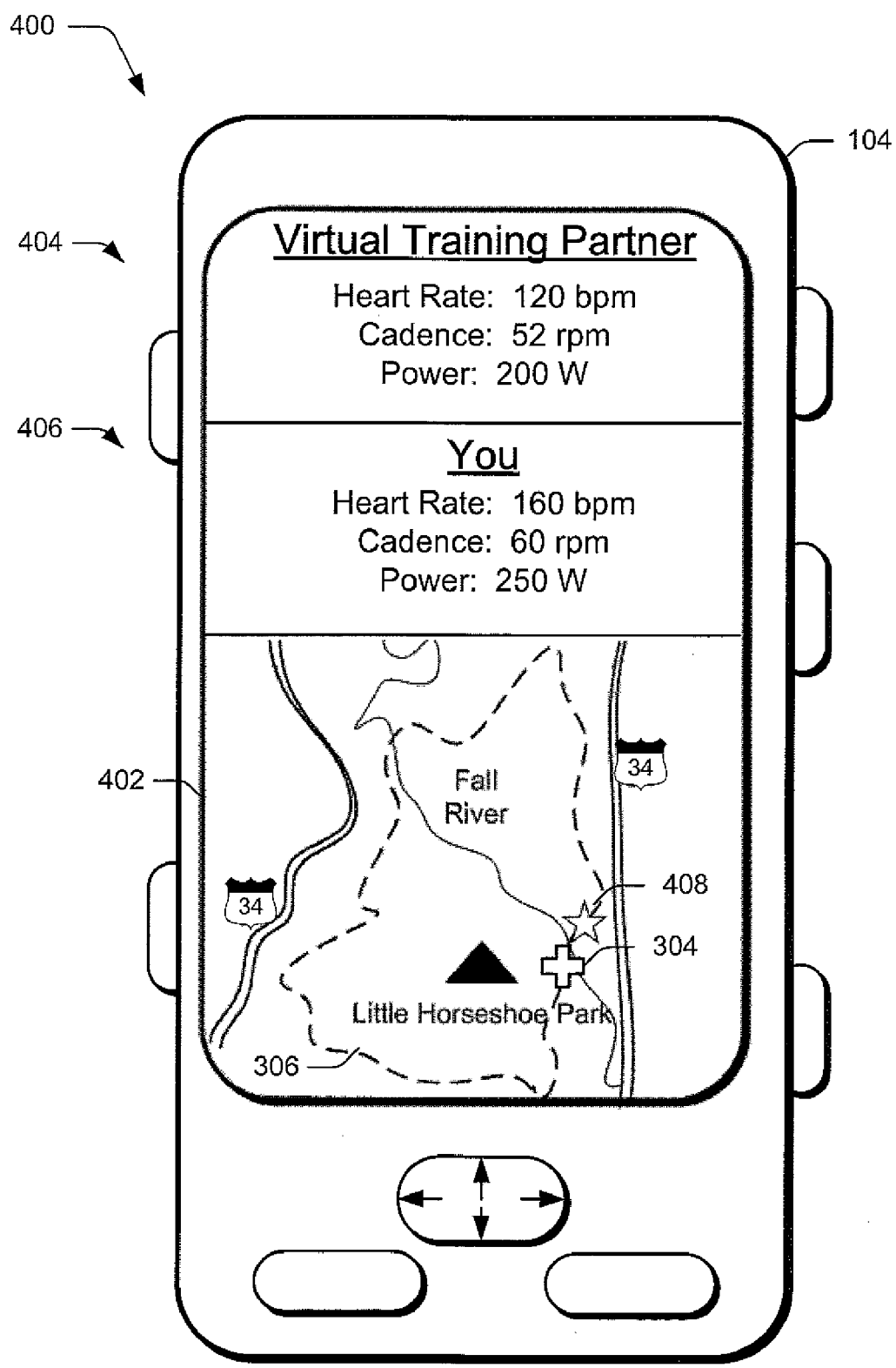
FIG. 4 is an illustration of an exemplary implementation of the bicycle computer of FIGS. 1 and 2 as outputting a map concurrently with training metrics of a virtual training partner and training metrics of a user of a bicycle having the bicycle computer.

FIG. 3 illustrates an exemplary implementation 300 of the bicycle computer 104 of FIGS. 1 and 2 as outputting a map 302 that includes a current geographical position 304 and a track 306. The map 302 as well as the indication of the track 306 and the current position 304 may be implemented in a variety of ways. For example, the map 306, with the indication of a current geographical position 304 may be output in real time as the bicycle computer is moved, which may also be performed concurrently with one or more training metrics, an example of which is shown in FIG. 4.

The map 302 of FIG. 3 is illustrated as a "routable basemap", which may be configured on a variety of ways. In a first non-limiting example, the basemap is a 13 MB autorouting basemap. This basemap may be improved by adding accuracy to the existing map features that are useful for bicyclists. For instance, cartography may increase resolution and reduce smoothing to create a basemap that more accurately displays the highways and major roads as well as bike trails and so on. The enhanced basemap, for example, may use up to 30 MB of internal memory.

The navigational features of the bicycle computer 104 may also be customized for the specific needs of cyclists. To avoid confusion, for instance, there may be a single choice for navigation on a main menu. This option may be called "Where To". Once "Where To" is selected, the bicycle computer 104 may display an option menu which may allow the user to select one of the following choices: "Follow History" "Saved Rides" "Back to Start" or "Find Places", each of which are described in greater detail below.

Follow History

The "Follow History" option may allow users to navigate using previous history tracks currently stored on the unit. Once the "Follow History" option is selected, the user may see a page where they can select from a list of their historical data.

After the user selects the history desired, the bicycle computer 104 may search the loaded maps to determine if all or a portion of the track 306 can be matched to the street data of the map. If it is determined that all or a portion of the track 306 can be map-matched, the track 306 may be broken into segments. The segments with map data available may then be converted to map-dependant segments. Once the user presses "start" to begin navigation, those segments of the track may display street names as shown in FIG. 3. Turn information may also be output using an auto-routing feature, e.g., turn-by-turn instructions. For those segments that do not have map-dependant data the unit may give point-to-point navigation. The bicycle computer 104 may also alert the user to "leave road" or "return to road" when a map-dependant segment connects to a segment without map data. If it is determined that no portion of the track 306 can be matched to the map data, point-to-point navigation may be used.

Saved Rides

"Rides" may be used as a generic term that represents a manual route or track loaded to the bicycle computer 104. The "Saved Rides" option may give users the ability to find and navigate these "rides". In some instance, rides may not contain the additional statistical information for racing the virtual training partner.

Navigating a saved ride may function similarly to the "Follow History" option with the exception that map-matching has already completed. Map-matching may occur when the ride is loaded to the unit. This may lower processing time and allow the user to begin navigating a saved ride nearly immediately upon selection.

Back to Start

A "Back to Start" option may automatically invert the active track making the start position the end point. Once this is accomplished, the unit may function the same as the "Follow History" option for navigation.

Find Places

A "Find Places" option allows users to search points of interest (POI) categories for routing purposes. For instance, a POI list may be populated with the basemap data.

Based on the map data available, the unit may decide whether it is better to navigate the user to the POI using the auto-routing feature or the point-by-point routing feature. If the user is currently navigating, the unit may give the user a choice to insert the POI as a via point.

FIG. 4 illustrates an exemplary implementation 400 of the bicycle computer 104 of FIGS. 1 and 2 as outputting a map 402 concurrently with training metrics 404 of a virtual training partner and training metrics 406 of a user of a bicycle having the bicycle computer 104. The training metrics 406 of the user of the bicycle are illustrated in FIG. 4 as "Heart Rate," "Cadence" and "Power," although a variety of other training metrics are also contemplated. Additionally, although the training metrics are output in a textual form in FIG. 4, the training metrics may be output in a variety of ways, such as via a graphical representation, use of color on a map, and so forth.

The training metrics 404 of the virtual partner are also illustrated in a textual form and include "Heart Rate," "Cadence" and "Power," although a variety of other training metrics are also contemplated. Additionally, a representation 408 is also included to indicate a virtual position of the virtual training partner along the track 306 in relation to the current position 304 of the bicycle computer. In this way, the user of the bicycle and the bicycle computer 104 is readily informed as to "where" the user is in relation to the virtual training partner. As previously described, the data used to configure the virtual training partner may be obtained from a variety of sources, such as through previously stored training metrics that are a function of geographical position, from a third party, and so on. A variety of other virtual training partner configurations are also contemplated, such as a three-dimensional "birds eye" view. Additionally, it will be appreciated that the user may select which of the training metrics for the virtual partner 404, user's training metrics 406, and map 402 are displayed by the bicycle computer 104. For example, the user may choose to have the bicycle computer 104 not display the training metrics 404 of the virtual training partner such that only the user's training metrics 406 are displayed with the map 402. Similarly, the user can choose to have only the map 402 displayed.

Figure 6:
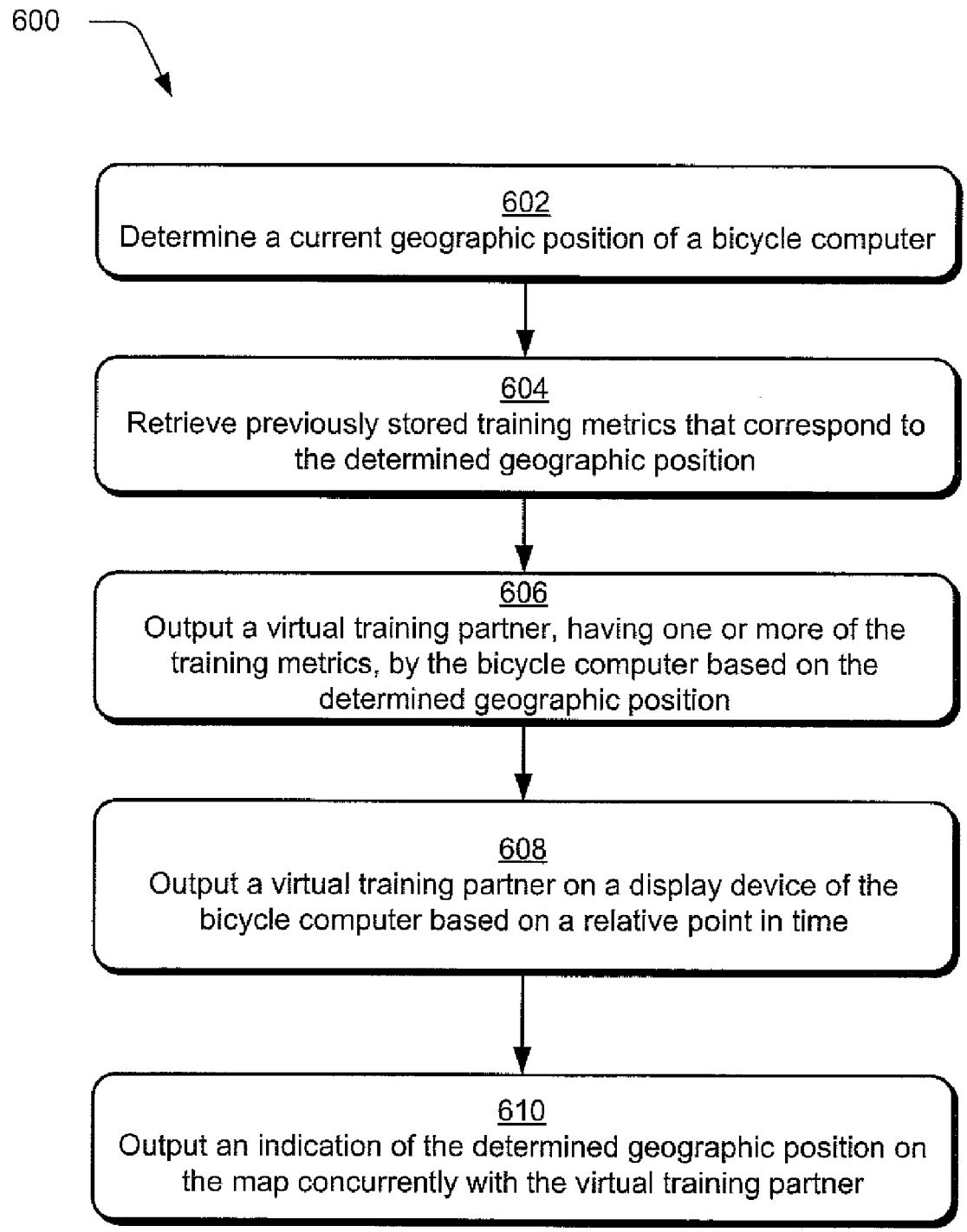
FIG. 6 is a flow diagram depicting a procedure in an exemplary implementation in which a virtual training partner is output by the bicycle computer of FIGS. 1 and 2.

Further discussion of virtual training partner may be found in relation to FIG. 6.

The following discussion describes bicycle computer use of position-determining techniques that may be implemented utilizing the previously described systems and devices. Aspects of each of the procedures may be implemented in hardware, firmware, or software, or a combination thereof. The procedures are shown as a set of blocks that specify operations performed by one or more devices and are not necessarily limited to the orders shown for performing the operations by the respective blocks. In portions of the following discussion, reference may be made to the environment 100 of FIG. 1, the system 200 of FIG. 2 and the bicycle computers of FIGS. 3 and 4.

Figure 5:
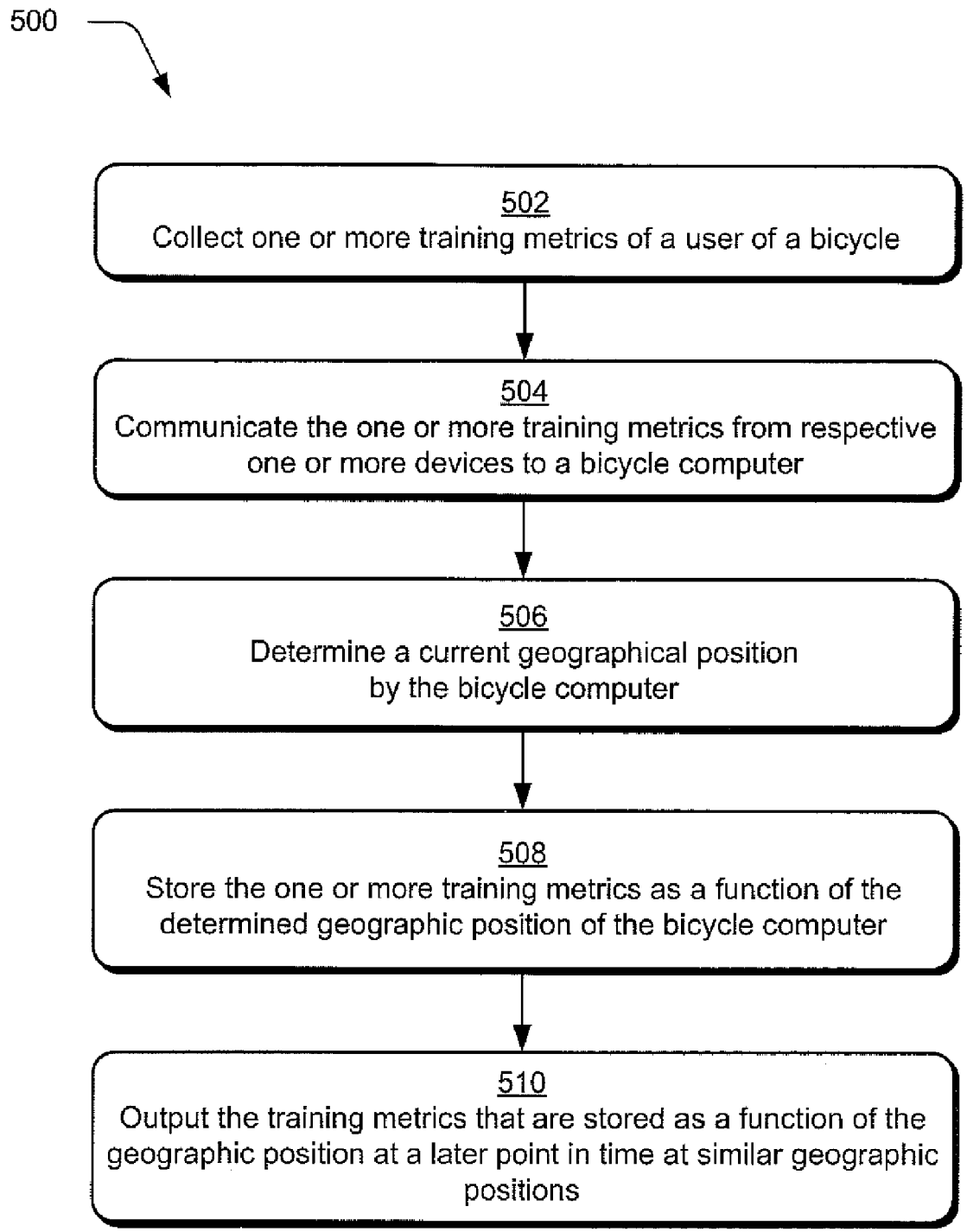
FIG. 5 is a flow diagram depicting a procedure in an exemplary implementation in which training metrics of a user of a bicycle are collected and stored as a function of a determined geographic position.

FIG. 5 depicts a procedure 500 in an exemplary implementation in which training metrics of a user of a bicycle are collected and stored as a function of a determined geographic position. One or more training metrics of a user of a bicycle are collected (block 502). For example, the heart rate monitor 206, cadence monitor 208, power monitor 210, and so on may collect training metrics. In another example, the bicycle computer 104 may derive the training metrics directly.

The one or more training metrics are communicated from respective one or more devices to a bicycle computer (block 504), such as over a wired or wireless connection.

A current geographical position is determined by the bicycle computer (block 506). For example, the bicycle computer may use GPS functionality to determine the current geographical position using the navigation module 122 and position data 124 as previously described in relation to FIG. 1. A variety of other techniques may also be utilized to determine geographical position, such as terrestrial based systems (e.g., wireless-phone based systems that broadcast position data from cellular towers), wireless networks that transmit positioning signals, and so on. For example, positioning-determining functionality may be implemented through use of a ground-based infrastructure, through one or more sensors (e.g., gyros, odometers, magnetometers), through one or more bicycle mounted sensors (e.g., wheel speed sensor, power meters or power sensors), use of "dead reckoning" techniques, and so on.

The one or more training metrics are stored as a function of the determined geographic position of the bicycle computer (block 508). For example, the training metrics may be sequentially indexed by geographical position within a "track" which may be later output.

The training metrics that are stored as a function of the geographic position are output at a later point in time at similar geographic positions (block 510). Continuing with the previous example, the user may save the training metrics as a track. The user may then select this track at a later time to train along the route. The bicycle computer, for instance, may output the training metrics as shown in FIG. 4 at similar geographic positions when encountered along the route. One example of such an output is through use of a virtual training partner, further discussion of which may be found in relation to the following figure. Additional position-determining functionality may also be employed, such as by use of navigation instructions.

FIG. 6 depicts a procedure 600 in an exemplary implementation in which a virtual training partner is output by the bicycle computer of FIGS. 1 and 2. A current geographic position of a bicycle computer is determined (block 602). As previously described, the geographic position may be determined in a variety of ways, one of which is through use of GPS functionality.

Previously stored training metrics that correspond to the determined geographic position are retrieved (block 604). For example, a user may have selected a track having a plurality of stored training metrics indexed by geographic position. One or more of the stored training metrics that correspond to the determined geographic position may then be retrieved from the track. A variety of other examples is also contemplated, which is not limited to the use of a track or a determined geographic position. For example, a relative time may be used to compare where the user currently is located along a track versus where the user was previously located along that track during a previous ride at that same relative point in time, further discussion of which may be found in relation to block 608.

A virtual training partner is output, having one or more of the training metrics by the bicycle computer based on the determined geographic position (block 606). The virtual training partner, for instance, may output training metrics which were obtained from the user during the previous ride, an example of which is illustrated in FIG. 4. In another instance, the training metrics of another user may be output, such as training metrics that were shared from a friend, purchased from a third-party website, and so on. A variety of other instances are also contemplated.

A virtual training partner, for instance, may also be output on a display device of the bicycle computer based on a relative point in time (block 608). For example, the user may start the track at a particular point in time. The bicycle computer may then track a relative point in time of a current user 304 as compared to a relative point in time of the virtual training partner 408 on the map 402. Further, an indication may be output of the determined geographic position on the map concurrently with the virtual training partner (block 610) on the map. Thus, the user may readily determine by comparing these indications as to how the user is progressing along the track 306 when compared with the virtual training partner. It should be noted that the training metrics 404 may still correspond to the current geographic position, while the indication on the map corresponds to the relative point in time such that the user may compare training metrics for like points along the track 306. A variety of other examples are also contemplated, such as indications of other objects that provide data to the bicycle computer to indicate a position of the other objects, further discussion of which may be found in relation to the following figure.

Figure 7:
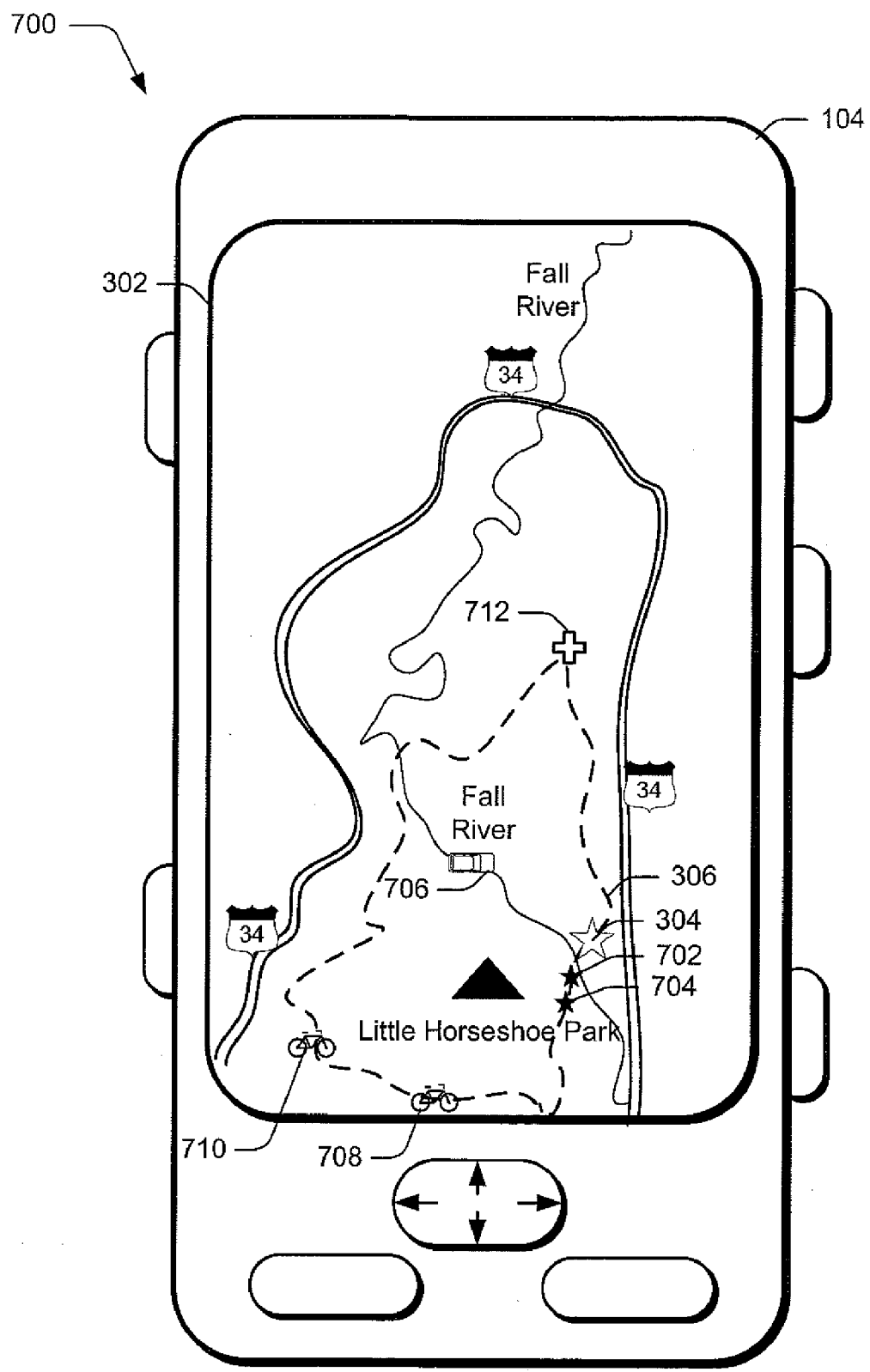
FIG. 7 is an illustration of an exemplary implementation of the bicycle computer of FIGS. 1 and 2 as outputting a map concurrently with representations of other users/bicycles, aid stations, and other objects that provide a position to the bicycle computer.

FIG. 7 is an illustration of an exemplary implementation 700 of the bicycle computer 104 of FIGS. 1 and 2 as outputting a map concurrently with representations of other users/bicycles, aid stations, and other objects that provide a position to the bicycle computer. The bicycle computer 104 is illustrated as outputting a map 302 that includes a current geographical position 304 and a track 306 as previously described in relation to FIG. 3.

The bicycle computer 104 is also illustrated as outputting representations of other objects that provide a position to the bicycle computer 104. A variety of representations may be output, such as representations of other riders 702, 704 of a team, a representation of a team car 706, representations of other riders not on the team 708, 710, an aid station 712, and so on. Thus, a user of the bicycle computer 104 may also be informed as to a position of other objects that are capable of transmitting a position to the bicycle computer 104.

Transmission of a position may be performed in a variety of ways. In a first example, the bicycle computer 104 may include functionality to determine the position of the other objects by the bicycle computer 104 itself. For example, the bicycle computer 104 may determine the position of the other object based on transmissions from the other objects, such as through use of radio beacons, timing signals, and so on. In another example, the bicycle computer 104 may "poll" the other objects using a challenge/response technique.

In yet another example, each of the other objects may include position-determining functionality (e.g., GPS) and transmit a determined position to the bicycle computer 104, may have a position manually input and then transmitted, and so on. Further, the transmission may include a variety of data, such as training metrics of the other rider 702, 704 on the team, e.g., for use by a team captain, team organizer, and so on.

Transmission may also be performed using a variety of wireless techniques, such as in accordance with one or more wireless protocols (e.g., 802.11, ANT, cellular, and so on), wireless radio, satellite, and so forth. Additionally, this transmission may be performed directly from the object to the bicycle computer 104 and/or indirectly, such as through a central data repository. The central data repository may also provide a variety of additional functionality, such as to categorize and further process data and then retransmit the processed data to the bicycle computer 104. A variety of other examples are also contemplated. Additionally, although these representations of objects are illustrated as output on a map 302 in the exemplary embodiment 700 of FIG. 7, these representations may be output using a variety of other techniques without departing from the spirit and scope thereof.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention.

What is claimed is:

1. A bicycle computer comprising:
   a housing;
   a display disposed on the housing; and
   one or more modules, disposed within the housing, to:
   determine the current geographic position and a current map segment type, the map segment being one of a street map-matched segment or a segment that is not street map-matched;
   calculate a route from the determined position to a destination;
   identify one or more positions along the calculated route where the current map segment type varies;
   output a map having an indication of the calculated route and the current geographic position in real time on the display;
   output an alert on the display if the current position is in proximity to one of the positions along the calculated route where the current map segment type varies; and
   output one or more training metrics of a user of a bicycle in real time on the display.

2. A bicycle computer as described in claim 1, wherein the training metrics are selected from a group consisting of heart rate, cadence and power output.

3. A bicycle computer as described in claim 1, wherein the modules are configured to receive at least one said training metric wirelessly from a device that collects data describing the at least one said training metric.

4. A bicycle computer as described in claim 3, wherein the device is configured to be attached to the user.

5. A bicycle computer as described in claim 1, wherein the one or more modules are further configured to output at least one training metric that was previously stored by the one or more modules that corresponds to the current geographic position.

6. A bicycle computer comprising one or more modules, disposed within a housing, to:
   determine the current geographic position and a current map segment type, the map segment being one of a street map-matched segment or a segment that is not street map-matched;
   calculate a route from the determined position to a destination;
   identify one or more positions along the calculated route where the current map segment type varies;
   store one or more training metrics of a user of a bicycle as a function of geographic position;
   output an alert if the current position is in proximity to one of the positions along the calculated route where the current map segment type varies; and
   output information related to the calculated route on a map in real time on a display.

7. A bicycle computer as described in claim 6, wherein the one or more training metrics are stored at predetermined intervals.

8. A bicycle computer as described in claim 6, wherein the information includes at least one of the training metrics.

9. A bicycle computer as described in claim 6, wherein the information includes at least one of the training metrics stored previously at the geographic position by the one or more modules.

10. A bicycle computer as described in claim 6, wherein the one or more modules are configured to determine the geographic position using one or more Global Positioning System (GPS) techniques.

11. A method comprising:
    determining a geographic position and a current map segment type of a bicycle computer, the map segment being one of a street map-matched segment or a segment that is not street map-matched;
    identifying one or more stored routes that correspond to the determined geographic position;
    identifying one or more positions along the calculated route where the current map segment type varies;
    calculating a route from the determined geographic position to a destination, the route including a portion of one or more stored routes; and
    outputting a virtual training partner, having one or more training metrics, by the bicycle computer based on the determined geographic position on a map in real time, wherein an alert is communicated for changes in map segment type.

12. A method as described in claim 11, wherein the virtual training partner is illustrated on a map that includes the determined geographic position.

13. A method as described in claim 11, further comprising outputting the determined geographic position by the bicycle computer.

14. A method as described in claim 11, further comprising outputting at least one said training metric of a current user of a bicycle having the bicycle computer concurrently with the virtual training partner.

15. A method as described in claim 11, wherein the determining is performed through use of one or more Global Positioning System (GPS) techniques.

* * * * *